United States Patent
Avitsian

(10) Patent No.: US 8,366,698 B2
(45) Date of Patent: Feb. 5, 2013

(54) INTERJUGULAR CATHETER AND METHOD

(75) Inventor: Rafi Avitsian, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/196,490

(22) Filed: Aug. 2, 2011

(65) Prior Publication Data

US 2013/0006078 A1  Jan. 3, 2013

Related U.S. Application Data

(62) Division of application No. 12/299,507, filed as application No. PCT/US2007/010521 on May 1, 2007, now Pat. No. 7,998,123.

(60) Provisional application No. 60/797,433, filed on May 4, 2006.

(51) Int. Cl.
*A61M 31/00* (2006.01)

(52) U.S. Cl. ......... 604/508; 604/507; 604/523; 604/264

(58) Field of Classification Search .................. 604/507, 604/508, 264, 284, 523
See application file for complete search history.

(56) References Cited

U.S. PATENT DOCUMENTS

| | | | | |
|---|---|---|---|---|
| 6,383,144 | B1 * | 5/2002 | Mooney et al. | 600/549 |
| 7,998,123 | B2 * | 8/2011 | Avitsian | 604/264 |
| 2003/0078645 | A1 | 4/2003 | Pigott | |
| 2005/0159673 | A1 * | 7/2005 | Dae et al. | 600/549 |

* cited by examiner

*Primary Examiner* — Laura Bouchelle
(74) *Attorney, Agent, or Firm* — Barnes & Thornburg LLP

(57) ABSTRACT

A catheter for insertion into a vascular system of a patient and for directing fluid flow includes a catheter body having a longitudinal axis and longitudinally spaced proximal and distal catheter ends with an intermediate catheter portion defined therebetween. An intermediate catheter outlet in the catheter body is located in the intermediate catheter portion and is spaced longitudinally from the proximal and distal catheter ends. A first lumen is defined within the catheter body and has longitudinally spaced proximal and distal first lumen ends with a reversing bend located therebetween, the first lumen providing fluid communication between the proximal catheter end and the intermediate catheter outlet. The reversing bend is located longitudinally between the intermediate catheter outlet and the distal catheter end. The reversing bend directs fluid flow to turn approximately 180° as the fluid flows through the first lumen. A method of using the catheter is also described.

7 Claims, 5 Drawing Sheets

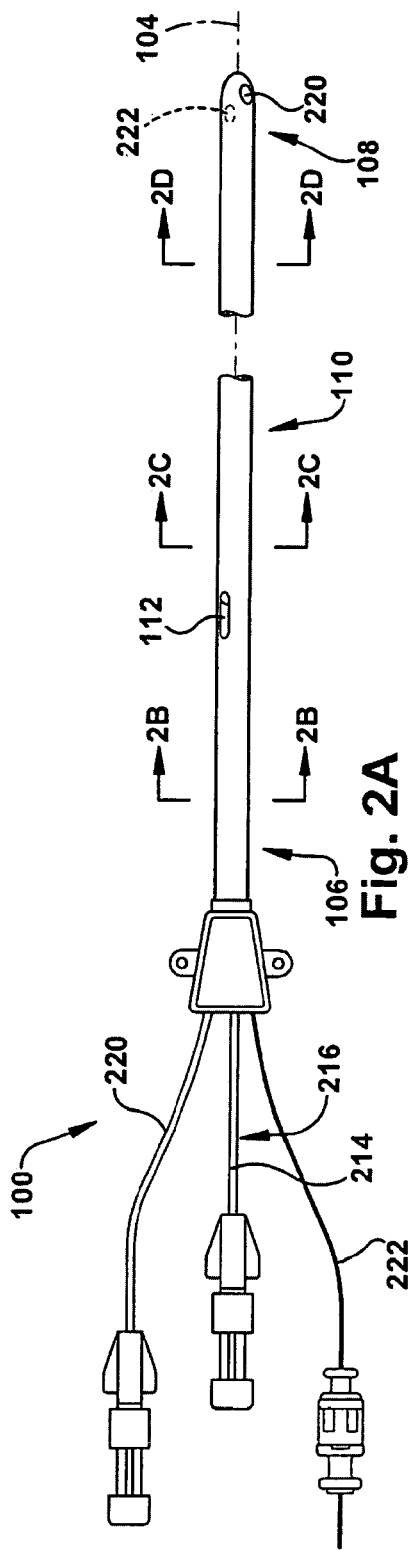
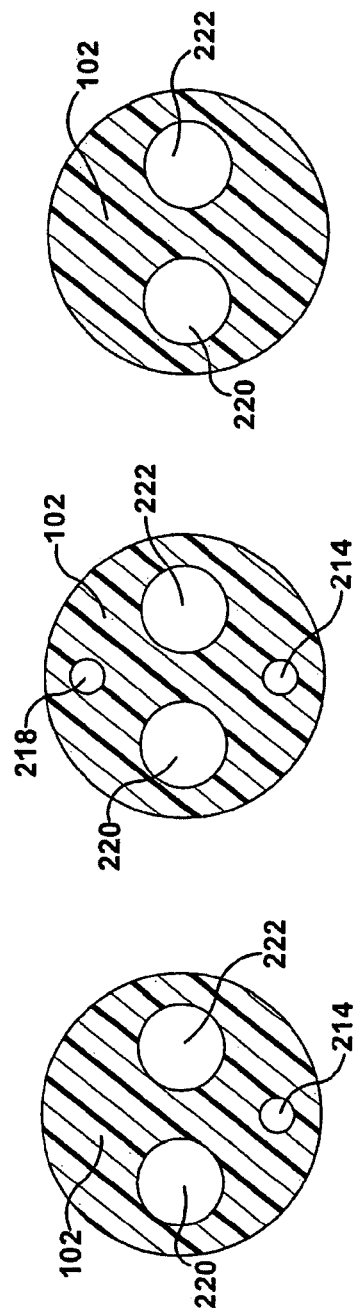
Fig. 2A
Fig. 2B
Fig. 2C
Fig. 2D

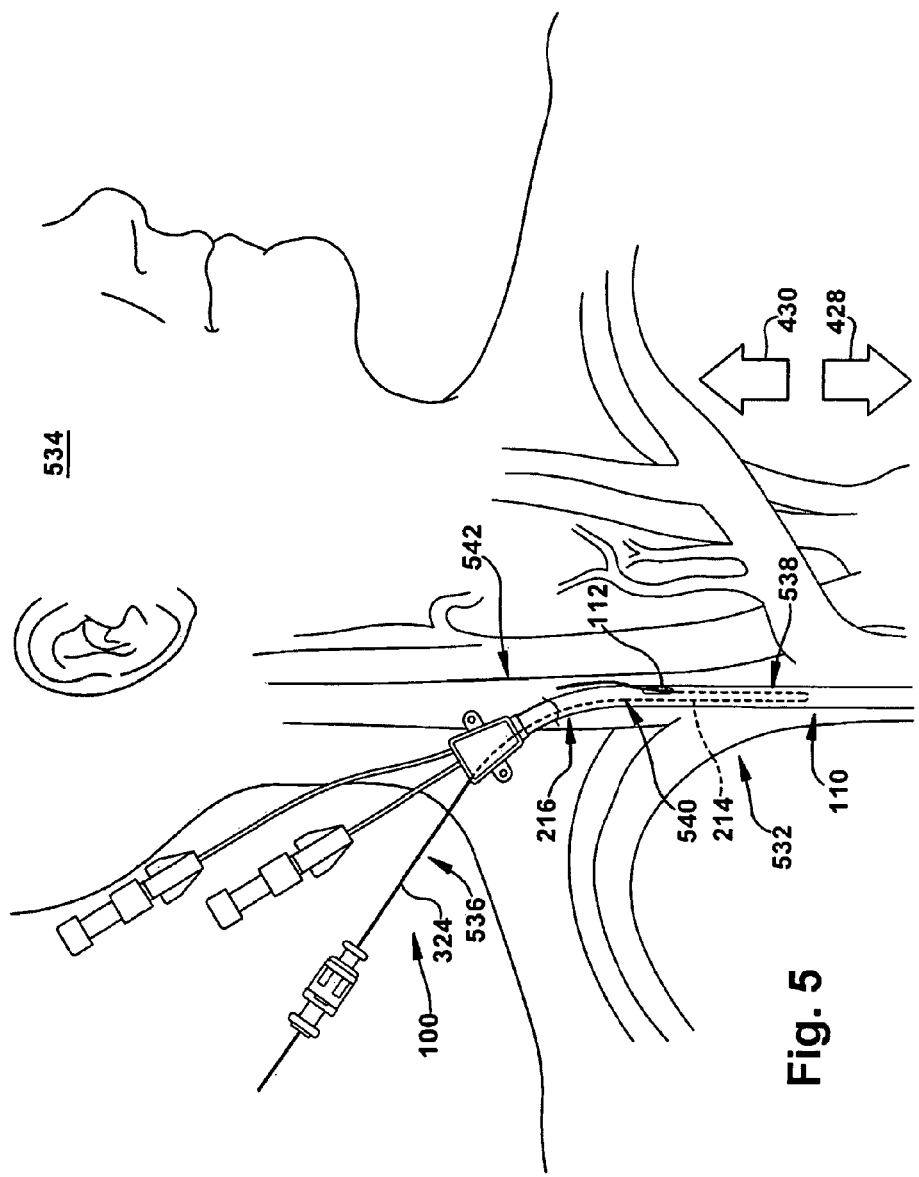

INTERJUGULAR CATHETER AND METHOD

RELATED APPLICATION

This application is a divisional of U.S. patent application Ser. No. 12/299,507, filed Nov. 4, 2008, now U.S. Pat. No. 7,998,123 which claims priority to PCT International Application No. PCT/US07/10521, filed 1 May 2007, which claims the benefit of U.S. Provisional Patent Application Ser. No. 60/797,433, filed May 4, 2006, the subject matter of which is incorporated herein by reference.

TECHNICAL FIELD

The present invention relates to an apparatus and method for use of a catheter and, more particularly, to a catheter for insertion into a vascular system of a patient and for directing fluid flow, blood flow for sampling, and for insertion of an oxygenation monitor through the catheter for continuous oxygen monitoring.

BACKGROUND OF THE INVENTION

During neurosurgical and other medical procedures, as well as for critically ill patients, monitoring brain oxygenation is a difficult but important task. One way to determine this oxygenation is through monitoring the amount of oxygenated blood returning from the brain through the internal jugular venous system. Monitoring the jugular venous oxygen saturation level can give an early warning of hypoxia of the brain. An oximeter catheter can be introduced through a catheter placed in the patient's jugular vein to continuously monitor the oxygenation of this blood.

Currently, catheters for measuring jugular venous oxygen saturation are inserted into the jugular vein in a cephalad (toward the head) direction, and the oximeter catheter can be introduced through this catheter to access the, jugular bulb. This differs from the regular method of access to the central venous system by anesthesiologists or critical care physicians, which is in a caudad (toward the feet) direction. Monitoring of blood oxygenation by accessing the blood using the caudad technique is not accurate since blood coming from the brain into the jugular vein mixes with blood from the head, neck, and upper extremities. On the other hand, a cephalad insertion directly into the jugular bulb is a complex and time-consuming procedure, with complications being possible. In addition, if there is a need for access to the central venous system, a caudad catheter may need to be inserted alongside the cephalad catheter to function as a regular central venous line. Such double catheterization may cause patient discomfort or trauma and a greater potential for infection.

Accordingly, it is desirable to provide a method and apparatus of an intrajugular catheter which is inserted by the conventional caudad method of jugular vein access but which also allows access to the jugular bulb.

SUMMARY OF THE INVENTION

According to one embodiment of the present invention, a catheter for insertion into a vascular system of a patient and for directing fluid flow comprises a catheter body having a longitudinal axis, and longitudinally spaced proximal and distal catheter ends with an intermediate catheter portion defined therebetween. An intermediate catheter outlet in the catheter body is located in the intermediate catheter portion and is spaced longitudinally from the proximal and distal catheter ends. A first lumen is defined within the catheter body and has longitudinally spaced proximal and distal first lumen ends with a reversing bend located therebetween, the first lumen providing fluid communication between the proximal catheter end and the intermediate catheter outlet. The reversing bend is located longitudinally between the intermediate catheter outlet and the distal catheter end. The reversing bend directs fluid flow to turn approximately 180° as the fluid flows through the first lumen.

The present invention further provides a method of accessing jugular blood of a patient. According to the inventive method, a catheter is provided, the catheter has a catheter body having a longitudinal axis and longitudinally spaced proximal and distal catheter ends with an intermediate catheter portion defined therebetween. An intermediate catheter outlet, located in the intermediate catheter portion, is spaced longitudinally from the proximal and distal catheter ends. A first lumen is defined within the catheter body and has longitudinally spaced proximal and distal first lumen ends with a reversing bend located therebetween. The first lumen provides fluid communication between the proximal catheter end and the intermediate catheter outlet. The reversing bend is located longitudinally between the intermediate catheter outlet and the distal catheter end. The reversing bend directs fluid flow to turn approximately 180° as the fluid flows through the first lumen. The distal catheter end is inserted into a jugular vein of a patient in a caudad direction. The intermediate catheter portion of the catheter is positioned within the jugular vein. The catheter is maintained within the jugular vein. A microcatheter having longitudinally spaced proximal and distal microcatheter ends with a microcatheter body located therebetween is provided. The distal microcatheter end is inserted into the proximal first lumen end. The microcatheter body is extended through at least a portion of the first lumen. The distal microcatheter end is extended through the intermediate catheter outlet and away from the first lumen in a cephalad direction.

BRIEF DESCRIPTION OF THE DRAWINGS

For a better understanding of the invention, reference may be made to the accompanying drawings, in which:

FIG. 2A is a partial side view similar to FIG. 1;

FIG. 2B is a cross-sectional view taken along the plane "B" of FIG. 2A;

FIG. 2C is a cross-sectional view taken along the plane "C" of FIG. 2A;

FIG. 2D is a cross-sectional view taken along the plane "D" of FIG. 2A;

FIG. 5 is a cutaway partial front view of a patient provided with an embodiment of the present invention.

DESCRIPTION OF EMBODIMENTS

Figure 1:
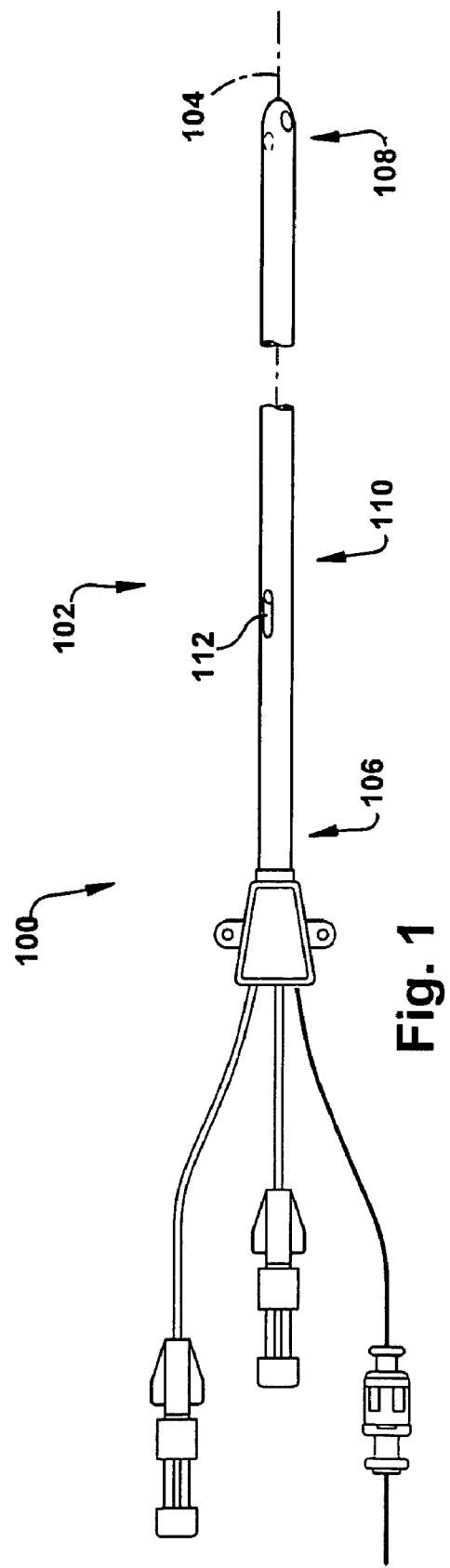
FIG. 1 is a partial side view of one embodiment of the present invention.

In accordance with the present invention, FIG. 1 depicts a catheter 100 for insertion into a vascular system of a patient and for directing fluid flow. As in all of the Figures, only a portion of the length of the catheter 100 is shown, for clarity. The external appearance of the catheter 100 is 'similar to that of known central venous access catheters. The catheter 100 has a catheter body 102 with a longitudinal axis 104 (only a portion shown, for clarity) and longitudinally spaced proximal and distal catheter ends 106 and 108, respectively, with an intermediate catheter portion 110 defined therebetween. An intermediate catheter outlet 112 is formed in the catheter body 102, located in the intermediate catheter portion 110, and spaced longitudinally from the distal end 108. The intermediate catheter outlet 112 is optionally adjacent the proximal end 106, as desired for a particular application of the catheter 100.

FIGS. 2A, 2B, 2C, and 2D depict a portion of the interior structure of the catheter 100. A first lumen 214 is defined within the catheter body 102 and has longitudinally spaced proximal and distal first lumen ends 216 and 218, respectively, as can be seen in the cutaway views of FIGS. 2B, 2C, and 2D. The first lumen 214 provides fluid communication between the proximal catheter end 106 and the intermediate catheter outlet 112. The term "fluid communication" is used throughout this description to indicate a certain type of relative arrangement and allows, but does not require, a fluid actually to be flowing at any given time between the features which are described as being in fluid communication.

The catheter 100 may include a second lumen 220 located within the catheter body 102 and fluidly isolated from the first lumen 214. The second lumen 220, when present, provides fluid communication between the proximal and distal catheter ends 106 and 108. The catheter 100 may include a third lumen 222 located within the catheter body 102 and fluidly isolated from the first and second lumens 214 and 220. The third lumen 222, when present, provides fluid communication between the proximal and distal catheter ends 106 and 108. Any number of lumens could be provided to the catheter 100, as desired for a particular application. The second and third lumens 220 and 222, when present, may provide functions similar to those in a known central venous line catheter inserted caudad (e.g. accessing blood for sampling, passing instruments therethrough, allowing endoscope access, facilitating injections to a desired location within the patient's body, allowing selective removal and insertion of catheters or other medical devices, and the like), and need not be further discussed.

Figure 3:
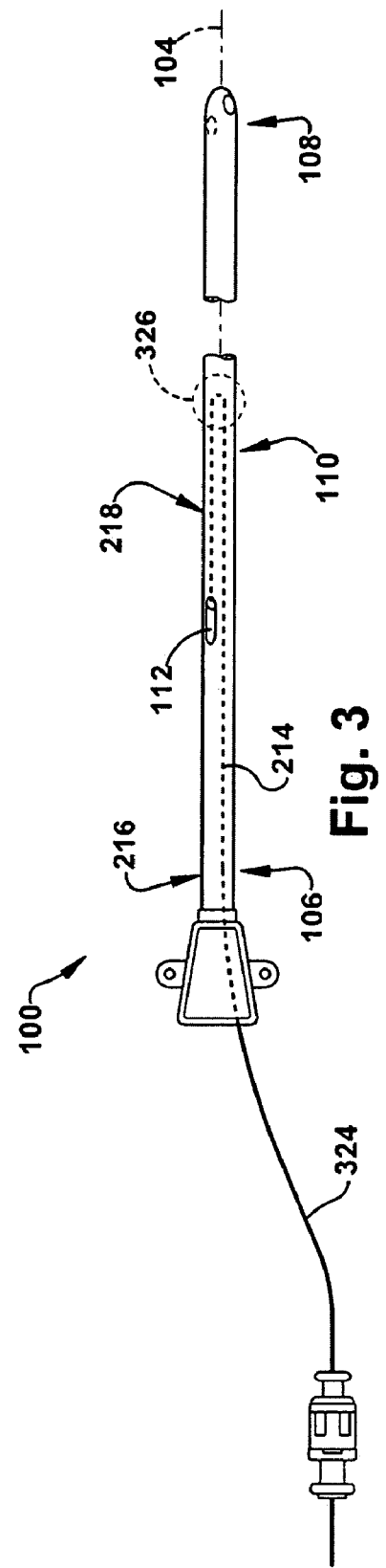
FIG. 3 is a cutaway partial side view similar to FIG. 1.

FIG. 3 is a partial cutaway view of the catheter 100. A microcatheter 324 is shown as being inserted into the first lumen 214 to show the configuration and structure of the first lumen 214 more clearly. A reversing bend 326 is located in the first lumen 214, between the proximal and distal first lumen ends 216 and 218. The reversing bend 326 is located longitudinally between the intermediate catheter outlet 112 and the distal catheter end 108. The reversing bend 326 directs fluid flow to turn approximately 180° as the fluid flows through the first lumen 214 and allows access to the jugular bulb as if the catheter 100 were inserted cephalad. The first lumen 214 may provide known catheter functions such as access to blood for sampling, passage for instruments therethrough, allowing endoscope access, facilitating injections to a desired location within the patient's body, allowing selective removal and insertion of catheters or other medical devices, and the like.

Figure 4:
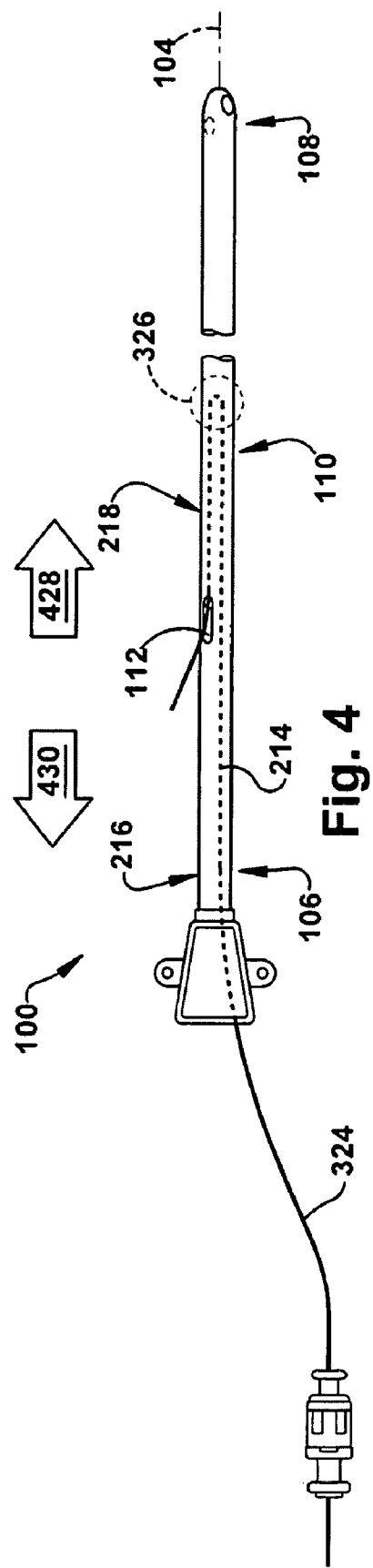
FIG. 4 is a cutaway partial side view similar to FIG. 1.

In the cutaway view of FIG. 4, the microcatheter 324 is shown as having been inserted into the proximal first lumen end 216, extending through the first lumen 214, and protruding from the distal first lumen end 218 through the intermediate catheter outlet 112. If the catheter 100 is inserted into the patient in a caudad direction (arrow 428), the microcatheter 324 protrudes from the distal first lumen end 218 in a cephalad direction (arrow 430) due to the function provided by the reversing bend 326. The microcatheter 324 may be an oximetric microcatheter 324 and the first lumen 214 is adapted to selectively access jugular blood of the patient as described below.

FIG. 5 depicts the catheter 100 as having been inserted into the jugular vein 532 of a patient 534 in the caudad direction 428. In use, the intermediate catheter portion 110 is positioned within the jugular vein 532 as desired. The catheter 100 is maintained within the jugular vein 532. A microcatheter 324 is provided, the microcatheter having longitudinally spaced proximal and distal microcatheter ends 536 and 538, respectively, with a microcatheter body 540 located therebetween.

The distal microcatheter end 538 is inserted into the proximal first lumen, end 216. The microcatheter body 540 is extended through at least a portion of the first lumen 214. The distal microcatheter end 538 is extended through the intermediate catheter outlet 112 and away from the first lumen 214 in a cephalad direction 430. The distal microcatheter end 538 may be extended further in a cephalad direction 430 and into a jugular bulb 542 of the patient 534. When the microcatheter 324 is an oximeter microcatheter, such positioning may provide an accurate indication of jugular venous oxygen saturation and thus aid in early detection of hypoxia of the brain. Optionally, blood is permitted to enter the first lumen 214 for other sampling or measurement purposes. For example, regardless of the presence or absence of a microcatheter 324 in the first lumen 214, suction can be applied to the proximal first lumen end 216 to draw a sample of blood through the intermediate catheter outlet 112 and out of the body through the proximal first lumen end 216.

The above steps may be reversed to remove the microcatheter 324 from the first lumen 214. Concurrently with the microcatheter 324 insertion through the first lumen 214, other microcatheters or similar medical devices could be inserted into the second and/or third lumens 220 and 222 in a similar manner. The above steps may be repeated as desired to re-insert the microcatheter 324 into the first lumen 214 without changing the position of the catheter 100 within the patient 534.

While aspects of the present invention have been particularly shown and described with reference to the preferred embodiment above, it will be understood by those of ordinary skill in the art that various additional embodiments may be contemplated without departing from the spirit and scope of the present invention. For example, any suitable catheters, microcatheters, or other devices may be selectively inserted into, and removed from, any of the first, second, and/or third lumens 214, 220, and 222 at any time and in any combination, whether or not the catheter 100 has been inserted into the patient. The catheter 100 could be used in other applications where there is a need to access portions of the body in a direction opposite the catheter insertion direction. A device or method incorporating any of these features should be understood to fall under the scope of the present invention as determined based upon the claims below and any equivalents thereof.

The method and apparatus of the present invention, when compared with other known apparatus and methods, have the advantages of allowing access to the jugular bulb and being insertible in a caudad direction.

Other aspects, objects, and advantages of the present invention can be obtained from a study of the drawings, the disclosure, and the appended claims.

Having described the invention, the following is claimed:

1. A method of accessing jugular blood of a patient, the method comprising the steps of:

providing a catheter having a catheter body having a longitudinal axis and longitudinally spaced proximal and distal catheter ends with an intermediate catheter portion defined therebetween, an intermediate catheter outlet in the catheter body, located in the intermediate catheter portion, and spaced longitudinally from the proximal and distal catheter ends, and a first lumen defined within the catheter body and having longitudinally spaced proximal and distal first lumen ends with a reversing bend located therebetween, the first lumen providing fluid communication between the proximal catheter end and the intermediate catheter outlet, and the reversing bend being located longitudinally between the intermediate catheter outlet and the distal catheter end, the reversing bend directing fluid flow to turn approximately 180° as the fluid flows through the first lumen;

inserting the distal catheter end into the jugular vein of the patient in a caudad direction;

positioning the intermediate catheter portion of the catheter within the jugular vein;

maintaining the catheter within the jugular vein;

providing a microcatheter having longitudinally spaced proximal and distal microcatheter ends with a microcatheter body located therebetween;

inserting the distal microcatheter end into the proximal first lumen end;

extending the microcatheter body through at least a portion of the first lumen; and extending the distal microcatheter end through the intermediate catheter outlet and away from the first lumen in a cephalad direction.

2. The method of claim 1, wherein the microcatheter is an oximetric microcatheter.

3. The method of claim 1, including the step of extending the distal microcatheter end into a jugular bulb of the patient.

4. The method of claim 1, wherein the reversing bend is located longitudinally between, and spaced apart from both of, the intermediate catheter outlet and the distal catheter end.

5. The method of claim 1, wherein the step of extending the microcatheter body through at least a portion of the first lumen includes the steps of:
  extending a first portion of the microcatheter body in a cephalad direction within the first lumen; and
  extending a second portion of the microcatheter body in a caudad direction through the first lumen, substantially parallel to the first portion of the microcatheter body.

6. The method of claim 1, wherein the reversing bend directs fluid flow to turn at an angle in the range of 170° to 190° as the fluid flows through the first lumen.

7. The method of claim 1, wherein the reversing bend directs fluid flow to turn at an angle of at least 135° as the fluid flows through the first lumen.

* * * * *